United States Patent
Schwarz et al.

(10) Patent No.: US 9,044,251 B2
(45) Date of Patent: Jun. 2, 2015

(54) FLUSHABLE CHUCK

(75) Inventors: Dieter Schwarz, Ebersbach (DE); Martin Schmideder, Leinfelden-Echterdingen (DE)

(73) Assignee: Josef Albrecht Bohrfutterfabrik GmbH & Co. KG, Wernau (DE)

( * ) Notice: Subject to any disclaimer, the term of this patent is extended or adjusted under 35 U.S.C. 154(b) by 1335 days.

(21) Appl. No.: 12/075,255

(22) Filed: Mar. 10, 2008

(65) Prior Publication Data

US 2008/0224427 A1    Sep. 18, 2008

(30) Foreign Application Priority Data

Mar. 17, 2007    (DE) .......................... 10 2007 012 859

(51) Int. Cl.
*A61B 17/16* (2006.01)
*A61B 19/00* (2006.01)
*B23B 31/12* (2006.01)
*A61C 1/14* (2006.01)
*B25G 3/22* (2006.01)

(52) U.S. Cl.
CPC ............. *A61B 17/162* (2013.01); *Y10T 279/34* (2015.01); *Y10T 279/17615* (2015.01); *Y10T 279/17632* (2015.01); *Y10T 279/17111* (2012.01); *A61B 2019/4868* (2013.01); *A61C 1/14* (2013.01); *B23B 31/1238* (2013.01); *B23B 31/1253* (2013.01); *B23B 2270/28* (2013.01)

(58) Field of Classification Search
CPC ... F16L 27/087; B23B 31/201; B23B 31/123; B23B 31/1253; B23Q 11/10
USPC ................ 279/20, 60–65; 408/56; 409/136
IPC ......................................................... B23Q 11/10
See application file for complete search history.

(56) References Cited

U.S. PATENT DOCUMENTS

| | | | | |
|---|---|---|---|---|
| 2,283,780 A | * | 5/1942 | Ahern | 4/255.01 |
| 2,996,061 A | * | 8/1961 | Miller | 408/59 |
| 3,012,921 A | * | 12/1961 | Vaughan | 438/748 |
| 3,136,059 A | * | 6/1964 | Nelson | 433/127 |
| 3,156,158 A | * | 11/1964 | Pamplin | 418/217 |
| 3,632,122 A | * | 1/1972 | Sessody | 279/4.09 |

(Continued)

FOREIGN PATENT DOCUMENTS

| | | |
|---|---|---|
| DE | 197 26 942 A1 | 1/1999 |
| DE | 198 48 371 A1 | 5/2000 |

(Continued)

OTHER PUBLICATIONS

Joachim Engel et al.; Method for Cleaning a Cutting Machine; Oct. 5, 2006; English Machine Translation of DE102005014096.*

*Primary Examiner* — Eric A Gates
*Assistant Examiner* — Bayan Salone
(74) *Attorney, Agent, or Firm* — R. S. Lombard; K. Bach

(57) ABSTRACT

In a chuck for medical applications, including a housing having a passage extending axially therethrough with clamping elements movable supported in the housing together with a drive structure for moving the clamping element into and out of a clamping position for the engagement and release of a rotating tool, a space is provided around the drive structure for moving the clamping elements and flushing passages are provided for flushing out the space around the drive structure and, in the process, cleaning all the components of the chuck.

16 Claims, 7 Drawing Sheets

(56) References Cited

U.S. PATENT DOCUMENTS

| | | | |
|---|---|---|---|
| 3,949,998 A * | 4/1976 | Dietzen et al. | 279/62 |
| 4,021,920 A * | 5/1977 | Kirschner et al. | 433/82 |
| 4,094,523 A * | 6/1978 | Derbyshire | 279/62 |
| 4,570,952 A * | 2/1986 | Heimbigner et al. | 279/20 |
| 4,627,628 A * | 12/1986 | Rohm | 279/20 |
| 4,669,933 A * | 6/1987 | Dye | 409/136 |
| 4,759,113 A * | 7/1988 | Hunkeler | 483/13 |
| 4,795,292 A * | 1/1989 | Dye | 409/136 |
| 4,822,218 A * | 4/1989 | Satoh | 409/136 |
| 5,002,442 A * | 3/1991 | Rutschle | 409/134 |
| 5,125,579 A * | 6/1992 | Eggert | 239/439 |
| 5,140,780 A * | 8/1992 | Lincoln | 451/444 |
| 5,230,389 A * | 7/1993 | Besson | 175/56 |
| 5,358,360 A * | 10/1994 | Mai | 408/61 |
| 5,474,235 A * | 12/1995 | Cole et al. | 239/431 |
| 5,580,197 A * | 12/1996 | Rohm | 408/240 |
| 5,884,842 A * | 3/1999 | Caine et al. | 239/251 |
| 5,904,451 A * | 5/1999 | Gerber | 408/56 |
| 5,934,689 A * | 8/1999 | Montjoy | 279/62 |
| 6,059,702 A * | 5/2000 | Winkler et al. | 483/13 |
| 6,073,522 A * | 6/2000 | Carnesi | 81/128 |
| 6,123,270 A * | 9/2000 | Hara | 239/8 |
| 6,135,679 A * | 10/2000 | Kazda | 408/57 |
| 6,200,073 B1 * | 3/2001 | Chung | 407/53 |
| 6,295,659 B1 * | 10/2001 | Sandness | 4/255.01 |
| RE37,484 E * | 12/2001 | Gerber | 408/56 |
| 6,449,975 B1 * | 9/2002 | Moreno | 62/314 |
| 6,572,310 B2 * | 6/2003 | Temple-Wilson | 408/56 |
| 6,808,342 B2 * | 10/2004 | Kress et al. | 409/136 |
| 6,857,344 B1 * | 2/2005 | Diller | 82/1.2 |
| 6,883,809 B2 * | 4/2005 | Rohm | 279/62 |
| 7,048,481 B2 * | 5/2006 | Sugata et al. | 409/136 |
| 7,134,812 B2 * | 11/2006 | Beckington | 408/56 |
| 7,144,207 B2 * | 12/2006 | Weigel | 408/56 |
| 7,172,542 B2 * | 2/2007 | Sato et al. | 483/1 |
| 7,261,021 B1 * | 8/2007 | Carnesi et al. | 81/128 |
| 7,478,979 B2 * | 1/2009 | Zhou et al. | 408/240 |
| 7,707,916 B2 * | 5/2010 | Pirseyedi | 81/128 |
| 7,727,132 B2 * | 6/2010 | Bahr | 483/13 |
| 7,785,046 B2 * | 8/2010 | Beckington | 408/56 |
| 7,866,641 B1 * | 1/2011 | Switzer | 269/20 |
| 2003/0020242 A1 * | 1/2003 | Mack | 279/60 |
| 2004/0004329 A1 * | 1/2004 | Schroeder | 279/60 |
| 2004/0020001 A1 * | 2/2004 | Lorincz et al. | 15/322 |
| 2004/0211449 A1 * | 10/2004 | Yokomoto et al. | 134/61 |
| 2005/0009679 A1 * | 1/2005 | Fujimoto et al. | 483/13 |
| 2005/0032615 A1 * | 2/2005 | Sato et al. | 483/13 |
| 2008/0183125 A1 * | 7/2008 | Issa | 604/26 |
| 2012/0042912 A1 * | 2/2012 | Saint | 134/99.1 |

FOREIGN PATENT DOCUMENTS

| | | |
|---|---|---|
| DE | 10 2005 014096 A1 | 10/2006 |
| DE | 102005014096 A1 * | 10/2006 |

* cited by examiner

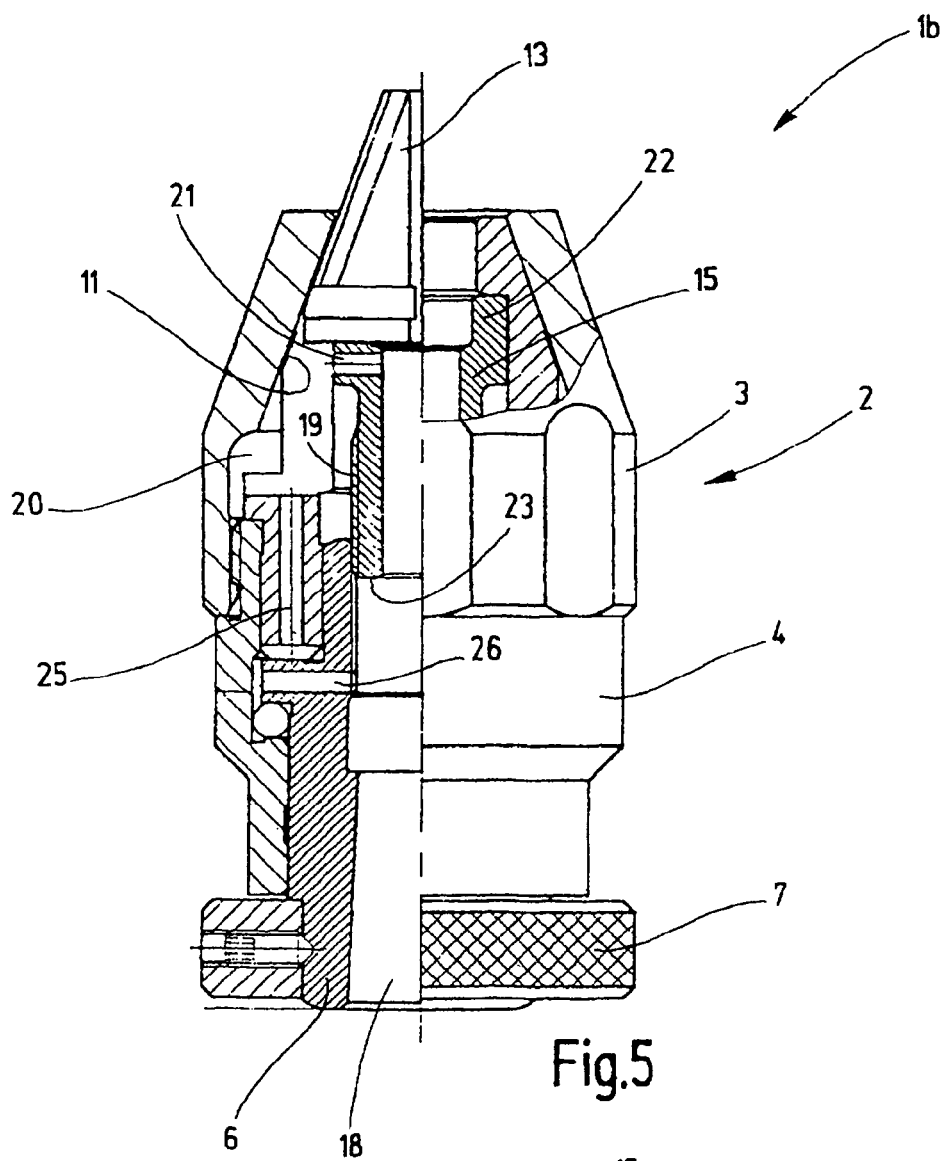
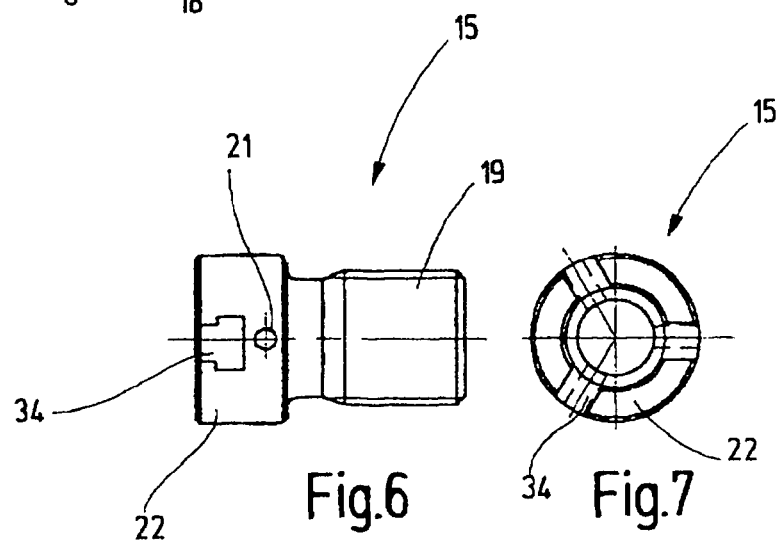

FLUSHABLE CHUCK

CROSS-REFERENCE TO RELATED APPLICATION

This application claims the priority benefits of German Application No. 10 2007 012 859.4-14 filed on Mar. 17, 2007.

BACKGROUND OF THE INVENTION

The invention resides in a drill or lathe chuck, particularly for medical equipment, comprising a housing with a central passage in which at least one clamping element is disposed and means for moving the clamping elements into, and out of, a clamping position.

Particularly in connection with surgery, but also in other medical areas, occasionally equipment is used wherein rotatable tools such as a drill or a milling cutter must be firmly engaged. To achieve this, drill or lathe chucks are used as they are known, for example, from DE 26 52 831 A1 and also from DE 27 35 358 A1.

During operation of such tools not only the tools, but also the chucks come into contact with body liquids and tissue of the patient. After use, the chucks must be cleaned for which suitable washing apparatus are provided.

Care must be taken during cleaning that the respective tool or chuck is cleaned in such a way that no residues remains.

It is therefore the object of the present invention to provide a drill or lathe chuck which satisfies high hygienic requirements.

SUMMARY OF THE INVENTION

A chuck for medical applications, including a housing having a passage extending axially therethrough with clamping elements movably supported in the housing together with a drive structure for moving the clamping element into and out of a clamping position for the engagement and release of a rotating tool, a space is provided around the drive structure for moving the clamping elements and flushing passages are provided for flushing out the space around the drive structure and, in the process, cleaning all the components of the chuck.

The chuck according to the invention comprises a housing with a through bore or passage which extends preferably concentrically with the axis of rotation of the chuck. The passage can be utilized to supply a tool engaged in the chuck with fluids such as air, salt solution or other treatment fluids. During cleaning of the chuck the passage can be used for the admission of cleaning fluids.

The drill or clamping chuck according to the invention comprises a drive with at least one drive element for moving at least one clamping element for firmly engaging or releasing a tool. The drive element may be, for example, a sleeve-like pressure spindle which is capable of axially acting on the clamping element. Preferably, it includes a through bore which extends concentrically with the axis of rotation of the chuck and from which a flushing channel branches off. As a result, the flushing channel extends, starting from the central passage within the housing and its inner components into internal spaces of the chuck which otherwise can hardly be reached by flushing fluids. The at least one flushing channel makes it possible to establish a flushing of the internal spaces of the chuck designed for cleaning the internal spaces and removing any tissue or tissue nests or residues of body liquids, such as blood lymph or similar. Preferably, several flushing channels are provided of which at least one extends to the interior spaces of the chuck and at least one extends outwardly from the interior spaces of the chuck. Preferably, the flushing channel includes a seat for accommodating a flushing nozzle. This seat may be formed, for example, by an annular shoulder via which the chuck is seated on a support surface of the flushing nozzle. Preferably, this seat is arranged between a flushing channel which conducts flushing fluid into the interior spaces of the chuck and a discharge channel which conducts the flushing fluid again out of the interior spaces of the chuck. The flushing channels improve the effectiveness of the cleaning procedures.

The location of the flushing channel and the discharge channel refers particularly to the axial position of the chuck.

Preferably, the housing of the chuck comprises several parts. It may comprise, for example, sleeve-like parts which are rotatable relative to one another for the clamping or release action of the clamping element. The clamping element may be a clamping jaw. The chuck may be, for example, in the form of a three-jaw chuck. For the movement of the three jaws, a drive element in the form of a pressure spindle may be provided. Preferably, the pressure spindle is in the form of a threaded sleeve including a central passage and a flushing channel branching off about radially. In the pressure sleeve, the seat for receiving the flushing nozzle mentioned earlier may be formed. Around the pressure spindle, an annular space is formed which extends within the chuck and which can be flushed by cleaning fluid. The flushing channel leads directly into this annular space. The discharge channel extends from the annular channel at a location which is spaced axially from the inlet of the flushing channel. As a result of the flushing of the space formed in the chuck, for example, concentrically with the central passage no hidden contamination nests can form in the chuck. It is particularly prevented that small infectious residues remain in gaps or cavities which then, during use of the chuck, for example, as a result of mechanical forces effective during operation, are released and enter the patient. Also flushing liquid residues can not be retained in the hollow spaces. The later release of cleaning fluids or dried-on residues thereof during use of the chuck is prevented.

The chuck is particularly designed for cooperation with a flushing nozzle, which extends essentially vertically, and onto which the chuck can be slipped. Flushing fluid discharged from the open end of the flushing nozzle flushes the chuck and reaches the hidden interior spaces as well as the outer surfaces, so that in this way it is cleaned particularly intensively.

Further details of advantageous embodiments of the invention will become apparent from the accompanying drawings.

BRIEF DESCRIPTION OF THE DRAWINGS

FIG. 5 shows another embodiment of the chuck in a partially sectional side view;

FIG. 6 is a side view of a pressure spindle provided in the chuck of FIG. 5;

FIG. 7 is an axial view of the pressure spindle of FIG. 6;

DETAILED DESCRIPTION OF PARTICULAR EMBODIMENTS

Figure 1:
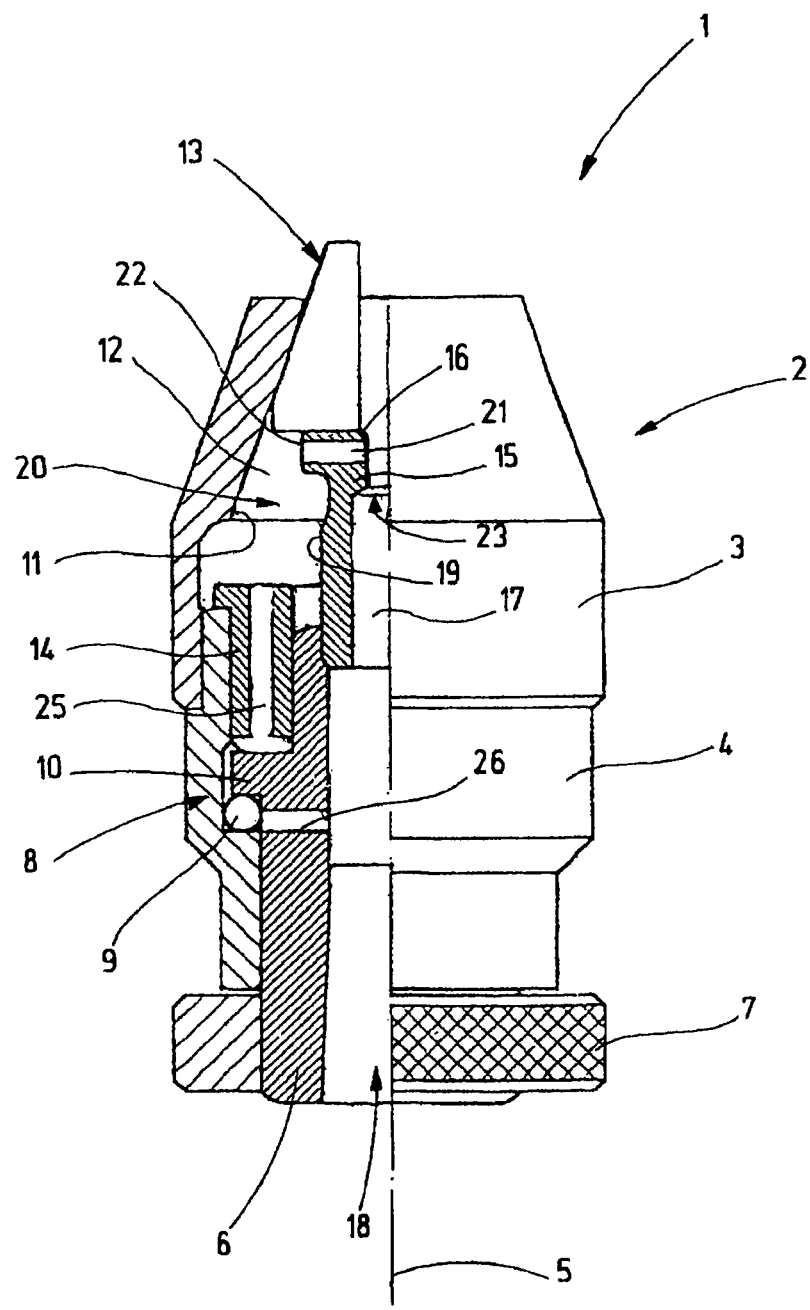
FIG. 1 shows a chuck according to the invention partially in a sectional side view.

FIG. 1 shows a chuck 1 for clamping medical drills, milling cutters or other driven rotating tools of medical equipment. The chuck 1 comprises a housing 2 which includes, in the shown embodiment, several parts. It comprises, for example, two sleeves or annular housing parts 3, 4 which are screwed together and are arranged concentrically with the axis of rotation 5 of the chuck 1. The housing 2 encloses a hollow space in which a sleeve-shaped carrier 6 is disposed. The carrier 6 is provided at its end projecting from the housing 2 with a knurled handling ring 7, which is connected to the carrier 6 for rotation therewith. The housing part 4 is disposed on the carrier 6 which little play and is rotatable relative thereto. For the support of the housing in radial and axial direction a ball bearing 8 is provided whose balls 9 roll between an annular shoulder of the housing part 4 and an annular shoulder 10 of the carrier 6.

In the housing 2, which is rotatably supported on the carrier 3, a clamping jaw support structure 11 is arranged which is part of the housing and is rotatable therewith. The clamping jaw support structure 11 comprises a front section which is formed by a conically narrowing section of the housing part 3 and has guide members 12 for supporting and guiding the clamping jaws 13. In FIG. 1 only one clamping jaw 13 is shown. However, preferably at least three such clamping jaws 13 are provided at locations spaced circumferentially 120° about the axis of rotation 5. In accordance therewith, at least three such guide structures 12 are provided which are formed by corresponding slots in the clamping jaw support structure 11. Alternatively, the clamping jaws 13 may also be supported directly by the housing part 3, for example, by corresponding grooves formed in the conical inner surface thereof.

The clamping jaw support member 11 has a socket section 14 which is connected to the housing 2 and is, for example, fixedly disposed thereon for rotation therewith.

The clamping jaws 13 are further engaged in radial slots of a pressure spindle 15, the radial slots being provided in the front face 16 thereof for guiding the clamping jaws 13. The pressure spindle 15 preferably has the form of a sleeve. It includes a central through-bore 17 which is part of a passage 18 extending concentrically with the axis of rotation 5 through the chuck 1. The pressure spindle 15 is provided at its outer circumference with an outer thread 19 which is in engagement with an internal thread of the carrier 6. The pressure spindle 15 is firmly coupled to the housing 2 for rotation therewith. The coupling can, for example, be established by way of the clamping jaws 13. Upon rotation of the housing 2 with respect to the carrier 6, the pressure spindle 15 can consequently be moved axially in clamping or release direction. In accordance therewith, the clamping jaws 13 are axially moved. Because of the conical shape of the front section of the housing part 2, a radical clamping movement is obtained at the same time.

Around the outer circumference of the pressure spindle 15 within the housing 2 an inner hollow space 20 is formed, into which contaminations, for example, in the form of blood, lymph liquids, tissue liquids and tissue particles may enter when the chuck 1 is used in surgical operations. For cleaning the hollow space 20 and any gaps or crevices in communication in this hollow space 20, the pressure spindle 15 includes a flushing channel 21 which branches off the passage 18. It is formed, for example, in the front flange 22 of the pressure spindle 15 by which the clamping jaws 13 are supported. Preferably several, that is two, three four or more such flushing channels 21 are formed in the flange 22. The flushing channels 21 may be radial bores. In close proximity of the flushing channels 21, preferably at the side remote from the clamping jaws 13, the through bore 17 of the pressure spindle 15 is provided with a step 23 by which the diameter of the through bore 17 becomes smaller. The through bore 17 becomes therefore smaller at the step 23 in the direction from the grasping ring 7 toward the clamping jaws 13. The step 23 serves as a stop for flushing wand 24 as shown in FIG. 2.

The chuck 1 may have additional flushing channels, such as a flushing channel 25 which extends in the clamping jaw support structure 11 parallel to the axis of rotation 5 and is in communication with a radial flushing channel 26 that branches off the ball bearing 8 and extends through the carrier 6 to the passage 18. If needed, several such flushing channels 25, 26 may be provided.

Figure 2:
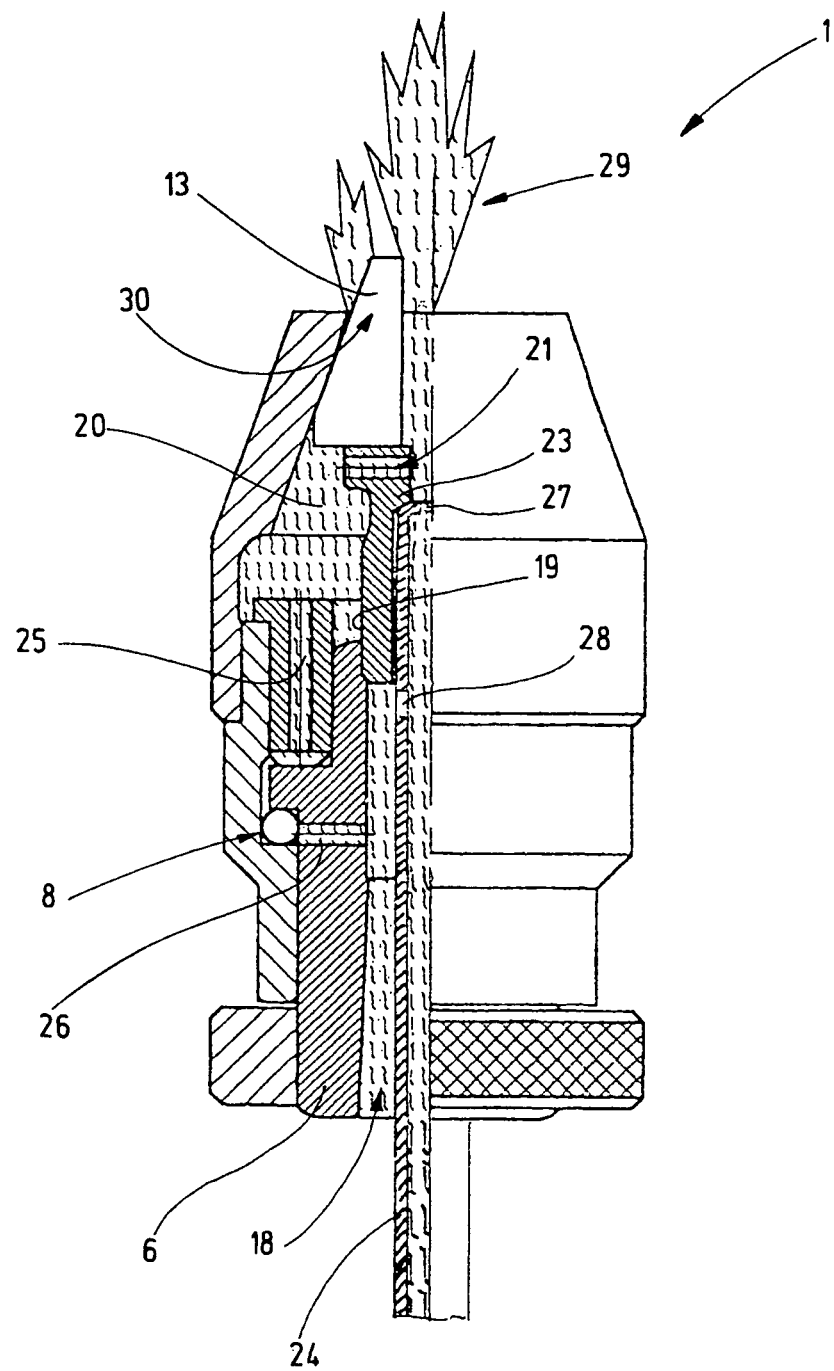
FIG. 2 shows the chuck of FIG. 1 during a flushing procedure.

The chuck 1 described, so far, can be thoroughly cleaned by means of an automatic cleaning apparatus. This is done as follows:

As shown in FIG. 2, a cleaning or washing apparatus for the chuck 1 may include a flushing wand 24 which is arranged essentially vertically and which supplies flushing fluid to the chuck 1. The flushing fluid is indicated in FIG. 2 by wavy dashed lines. A respective washing apparatus may have a plurality of such wands. The wand 24 is provided at its upper end with a flushing fluid discharge opening 27. The diameter of the flushing wand 24 is so selected that it can be inserted through the passage 18 up to the step 23 so that the step 23 is seated on the front face of the flushing fluid wand 24. The flushing fluid wand 24 may additionally be provided at its circumference with one or several flushing fluid discharge openings 28. Flushing fluid is constantly pumped through the flushing wand 24 and is discharged via the fluid discharge openings 27, 28. The fluid discharged via the flushing fluid front end opening 27 flows through the space in which the clamping jaws 13 are disposed and exits the chuck 1 at the front end thereof. This is symbolized in FIG. 2 by the flushing fluid fountain 29. The flushing fluid flows around the clamping jaws 13 and thoroughly cleans the front end of the chuck 1 and the outer surfaces of the clamping jaws 13. At the same time the flushing fluid flows through the flushing channel 21 into the hollow space 20 which thereby is filled with flushing fluid. From there the flushing fluid flows through the flushing channel 25 to the ball bearing 8 to clean it and then exits via the flushing channel 26. In the same way, flushing fluid can flow out of the hollow space 20 via the thread structure between the external thread 19 of the pressure spindle 15 and the carrier 6 into the passage 18 and, in this way, clean out hidden gaps such as the thread structure.

Preferably; the cleaning procedure of the chuck 1 is performed with the clamping jaws 13 in a predetermined position. To this end, the clamping jaws 13 may be provided with a special mark 30 which the operator must bring to a certain desired position before the beginning of the cleaning procedure. The mark 30 may be, for example, a line engraved into one or all the clamping jaws 13 or another mark which must be brought into alignment with the front face of the housing 1.

Figure 3:
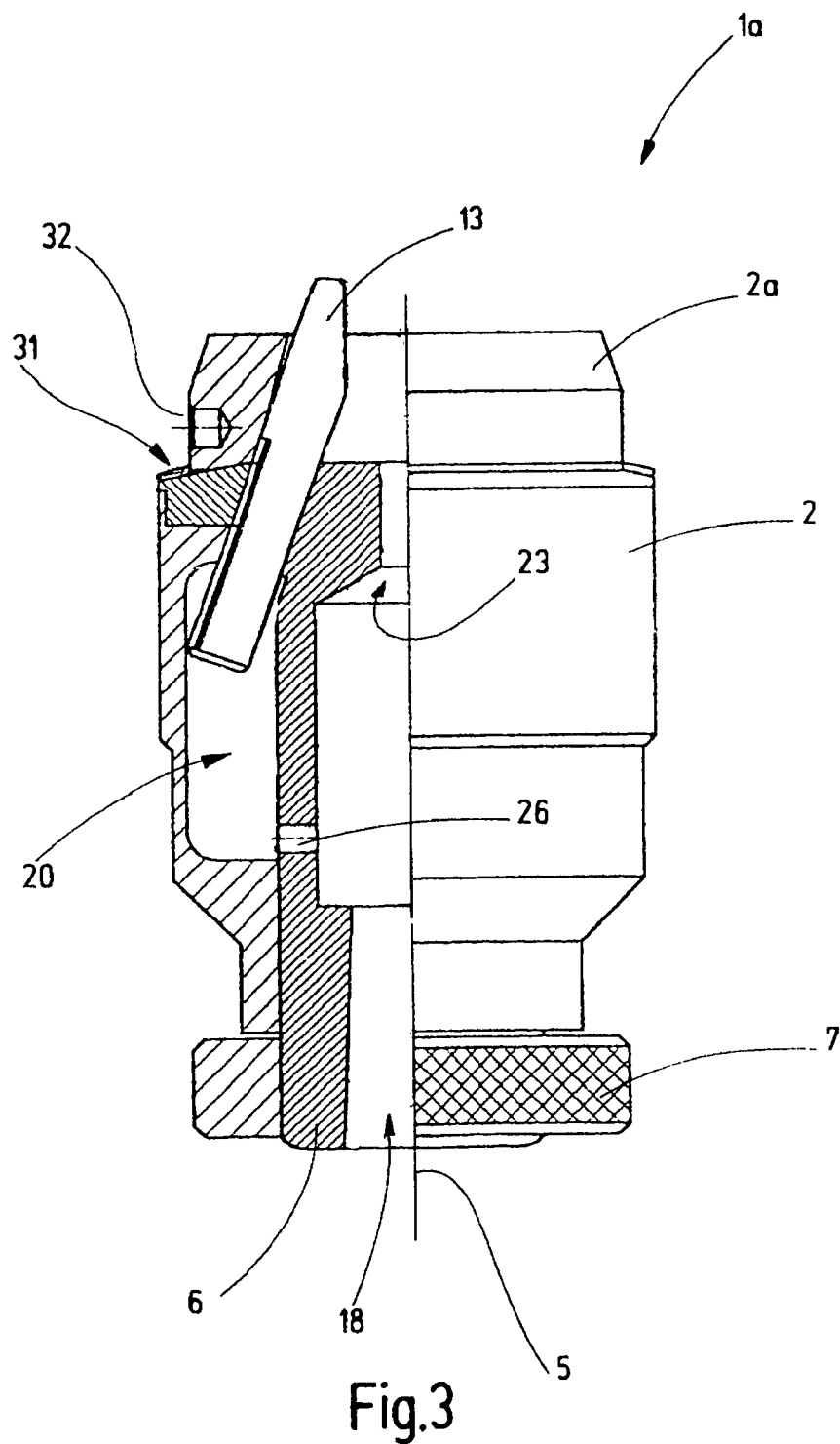
FIG. 3 shows a modified embodiment of the chuck according to the invention in a partially sectional side view.

FIG. 3 shows a modified embodiment of the chuck 1. As far as, this embodiment is structurally or functionally the same as the embodiment of the chuck 1 described above, the same reference numerals are used and reference is made to the description of the previous embodiment. Different from the chuck described before which operated by hand, the chuck 1*a* shown in FIG. 3 is operated into and out of its clamping state by means of a clamping wrench. Its housing 2 is rotatably supported by the carrier 6 on which the clamping jaws 13 are supported, so as to be movable along a line which is inclined with respect to the center axis 5. The carrier 6 is provided at the outside thereof with gear structure 31 which can be engaged by a bevel gear. At a housing section 2*a* near the gear structure 31 a bore 32 is provided into which the shaft end of the bevel gear can be inserted. The bevel gear is then in engagement with the gear structure. It is part of an operating wrench by which, upon its rotation the housing part 2*a* can be rotated relative to the carrier 6. In this way, the clamping jaws 13 can be moved axially in either direction which they also move radially inwardly or outwardly for the engagement or the release of a tool.

Also in this embodiment, a central passage 18 is provided which extends from one end of the carrier 6 to the other end thereof. Within the passage 18, again a step 23 is provided which serves as a seat for the flushing wand 24 (FIG. 2). The carrier 6 is provided with a flushing channel 26 via which flushing fluid can flow from the hollow space 20 into the passage 18.

Figure 4:
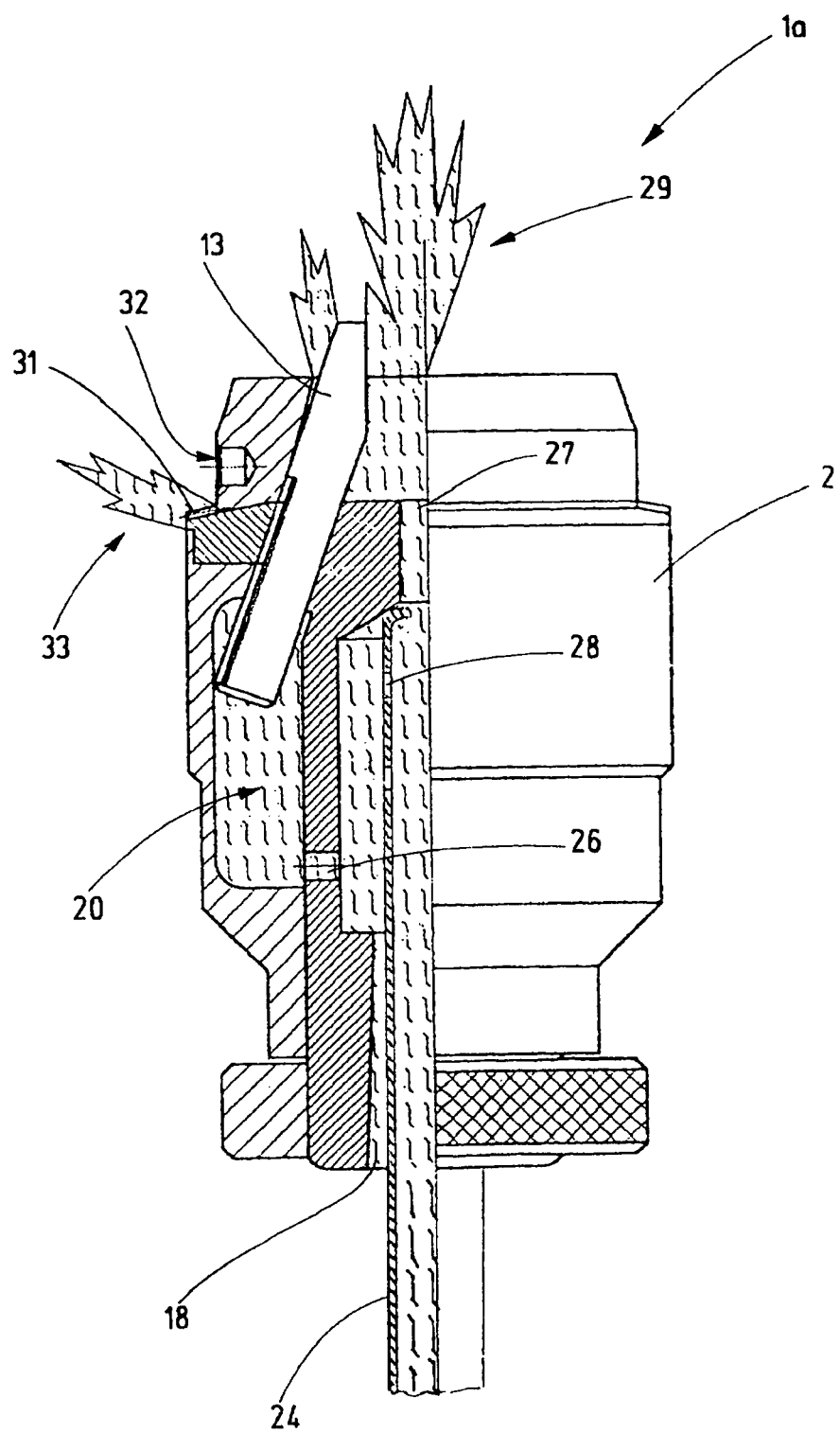
FIG. 4 shows the chuck of FIG. 3 during a flushing procedure.

For cleaning the chuck 1*a*, the chuck is placed onto the flushing wand 24 as shown in FIG. 4. The flushing fluid discharged from the flushing fluid discharge opening 27 flows around the ends of clamping jaws 13 projecting from the housing 2 and forms a flushing fluid fountain 29. At the same time, the flushing fluid enters, via housing gaps, the hollow space 20 and also exits as a flushing fluid fountain 33 at the gear structure 31. The relatively large amount of flushing fluid reaching the hollow space 20 cleans all the gaps along the clamping jaws 13 and returns to the passage 18 from which it exits the chuck 1.

After the cleaning procedure, the chuck 1*a* is cleaned also in the deep gaps thereof.

Another modified embodiment is shown in FIG. 5 on the basis of the chuck 1*b*. The chuck again comprises three clamping jaws 13 and is designed for manual operation by rotating the housing 2 with respect to the handling ring 7. The step 23 is in this case formed by the lower front end of the pressure spindle 15 which, for clarity, is shown separately again in FIGS. 6 and 7. As apparent therefrom, it is provided at its front flange 22 with guide grooves 34 and with at least one flushing channel 21. The operation is the same as described in connection with FIG. 1 and FIG. 2.

Figure 8:
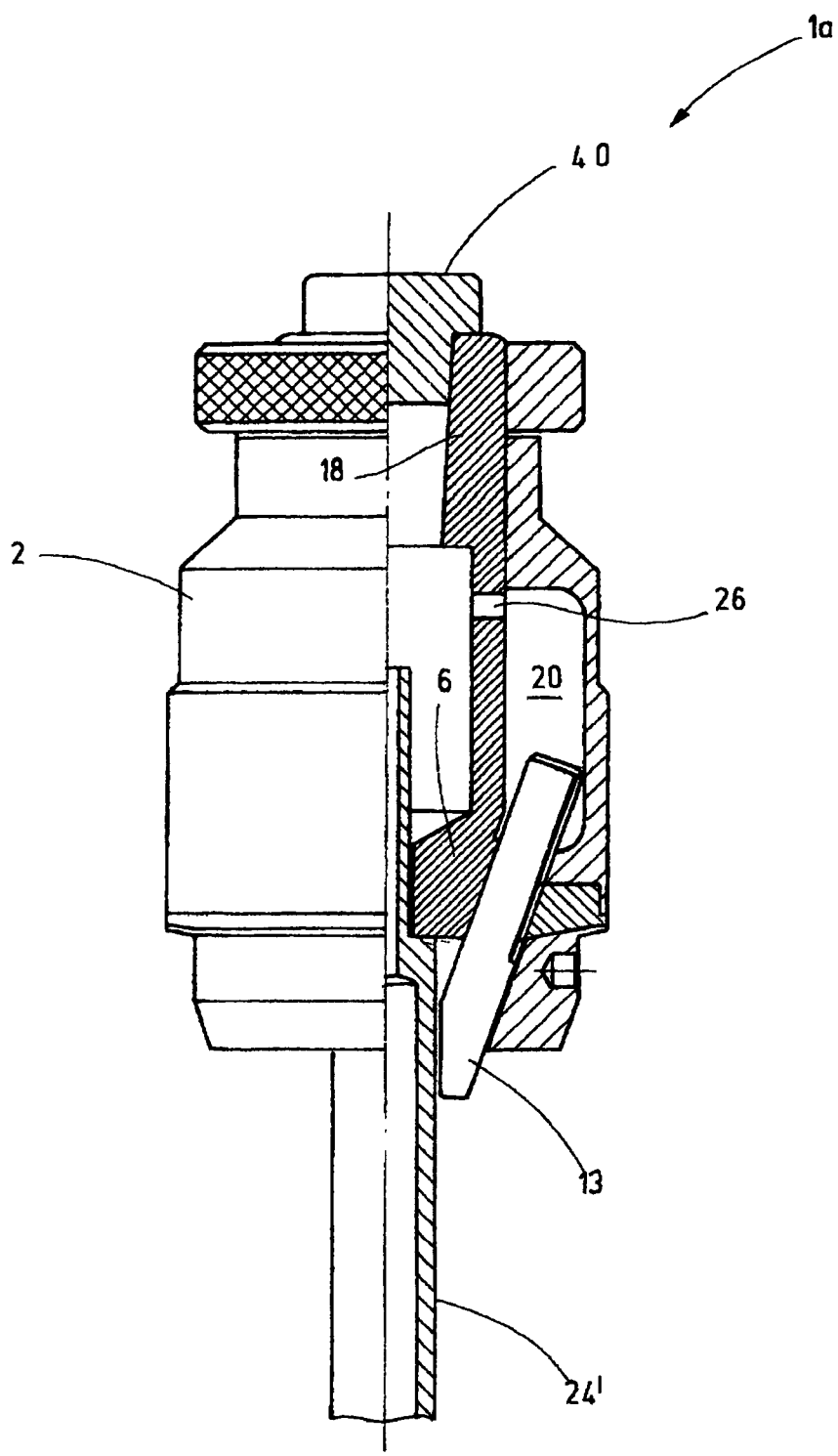
FIG. 8 shows the chuck of FIG. 3 during a modified flushing procedure.

FIG. 8 discloses a modified flushing arrangement for the chuck 1a of FIG. 3. The chuck 1*a* is placed onto the flushing wand 24' with opening for receiving the tools oriented downwardly and accommodating the wand 24'. In this way, the interior of the chuck is filled with flushing fluid as described earlier. At its mounting end, the chuck 1*a* or, respectively, its housing 2 is closed by a suitable closing member 40, for example, in the form of a plug. The flushing channel 26 now serves for conducting flushing fluid to the hollow space 20 from which the flushing fluid then flows out along the clamping jaws 13.

The flushing procedure for the chuck 1*a* and the hollow space 20 thereof is considered to be particularly efficient.

Figure 9:
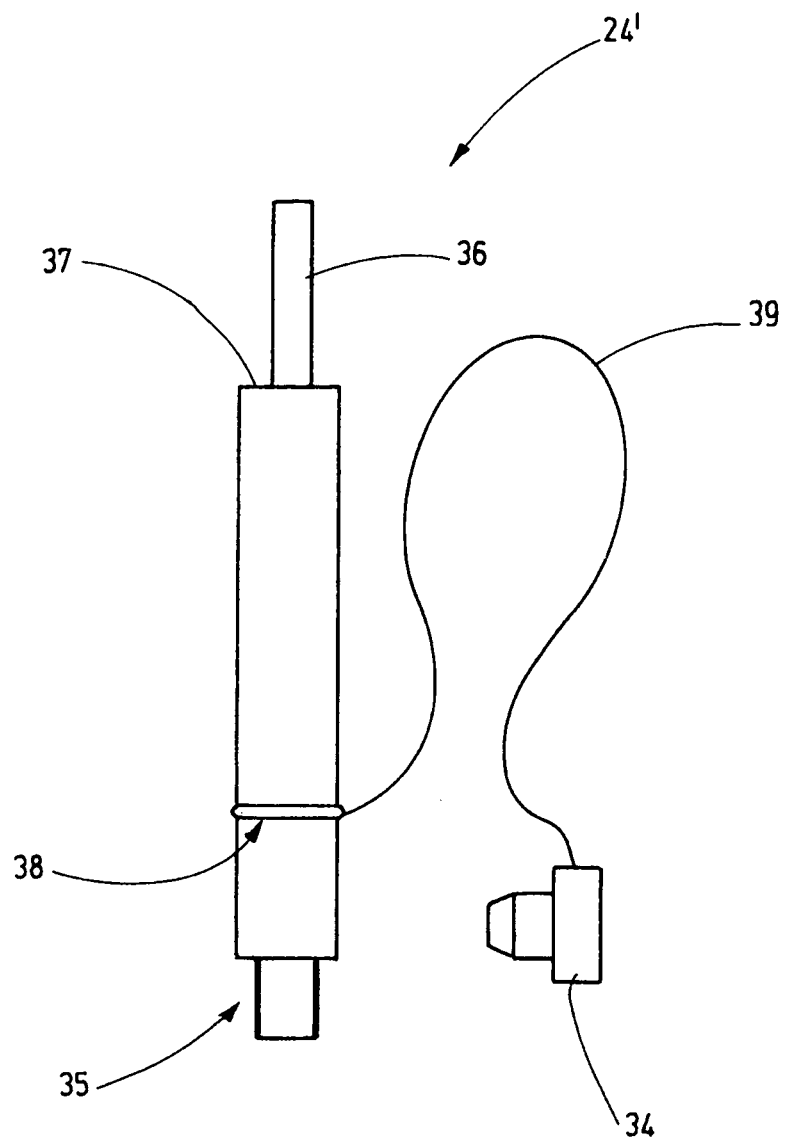
FIG. 9 shows a flushing nozzle for a cleaning apparatus for accommodating the chuck according to the invention.

FIG. 9 shows the flushing wand 24' above. It is formed by a tube of a special shape. At its lower end, as shown in FIG. 9, the flushing wand 24' includes a connecting structure, for example, in the form of a threaded section 35. This section can be threaded into a hollow member by way of which flushing fluid is supplied by the clean apparatus to the flushing wand 24'. In place of the threaded section 35, of course, other connecting means may be provided, such as, for example, bayonet connections.

At the upper end of the flushing wand 24', a tube extension 36 is provided which has a smaller diameter than the other part of the flushing wand 24'. The tube extension 36 projects from an annular shoulder 37 which forms a step and also an abutment surface for supporting the chuck 1*a* or the chuck 1. The annular shoulder 37 forms a seat, for the carrier 6 which abuts the annular shoulder 37 in a flow restricting or sealing manner.

The flushing wand 24' may also be connected to the closing element 40 to prevent it from being lost. The closing element is connected to the flushing wand 24', for example, by a cord, a chain or a flexible plastic piece. The flushing wand 24' may be provided, for example, with an annular groove 38 into which a plastic material is injected to fill the groove and form a loop from a plastic line 39 extends to the closing element 40 which may consist of the same plastic material. The loop filling the annular groove 38, the line 39 and the closing element 40 may be an integral plastic part.

A chuck 1 provided for medical applications includes, at least an internal hollow space 20 which may be arranged concentrically with a passage 18 extending through the chuck and is open at both ends and is also in communication with any gaps or crevices in the chuck. At least one flushing channel 21 and/or 26 is provided specifically for flushing the internal hollow space 20 during cleaning of the chuck thereby improving the hygiene.

What is claimed is:

1. A medical chuck (1) for medical apparatus including rotating tools for use on a patient, comprising a housing (2) having an interior having spaces that may become contaminated during use of the medical chuck (1), at least one clamping jaw (13) movably supported in the housing (2) and means for moving the at least one clamping jaw (13) into, and out of, clamping positions extending beyond the housing (2) and including at least one drive element (15, 6), the means for moving the at least one clamping jaw (13) housed within the housing (2), means for hygienically liquid flushing the medical chuck (1) including all of the spaces of the interior of the housing (2), the at least one clamping jaw (13) and the at least one drive element (15, 6) of retained bodily liquids and tissues of a patient after use of the medical chuck (1), wherein the means for hygienically liquid flushing the medical chuck (1) including all spaces of the interior of the housing (2), the at least one clamping jaw (13) and the at least one drive element (15, 6) of retained bodily liquids and tissues of a patient comprises the housing (2) having a central liquid flushing passage (18) extending axially therethrough, the at least one drive element (15, 6) at least partially surrounded by a liquid flushing chamber formed by a hollow space (20), the at least one drive element (15, 6) including at least one liquid flushing channel (21, 25, 26) in fluid communication between the central liquid flushing passage (18) and liquid flushing chamber (20), a removable hollow flushing wand or nozzle (24, 24') including an upper end having a first liquid discharge opening (27) in insertable relationship with the central liquid flushing passage (18) and upon insertion of the upper end of the removable hollow flushing wand or nozzle (24, 24') in the central liquid flushing passage (18) the first liquid discharge opening (27) in liquid communication with the central liquid flushing passage (18) and at least the hollow space (20), the removable hollow flushing wand or nozzle (24, 24') for insertion in the central liquid flushing passage (18) after use of the medical chuck (1) on the patient for carrying hygienic flushing liquid for thorough hygienic liquid flushing of the medical chuck (1) of retained bodily liquids and tissues of the patient including all spaces of the interior of the housing (2), a step (23) in operative position in the central liquid flushing passage (18), the removable hollow flushing wand or nozzle (24, 24') upon insertion into the central liquid flushing passage (18) in seated relationship with the step (23), the step (23) is formed axially between first and second liquid flushing channels (21 and 26), and, a first liquid flushing channel (21) is a flushing liquid supply channel and a second liquid flushing channel (26) is a flushing liquid outflow channel.

2. The medical chuck (1) according to claim 1, wherein the housing (2) comprises at least two parts (3, 4) in operative relationship with each other and concentrically arranged with an axis of rotation (5) of the medical chuck (1).

3. The medical chuck (1) according to claim 1, wherein the housing (2) includes several clamping jaws (13) which are arranged around the central liquid flushing passage (18).

4. The medical chuck (1) according to claim 1, wherein the drive element (15) is in engagement with the at least one clamping jaw (13) for moving the clamping jaw (13).

5. The medical chuck (1) according to claim 4, wherein the drive element (15) is a pressure spindle in the form of a threaded sleeve.

6. The medical chuck (1) according to claim 5, wherein the first liquid flushing channel (21) is formed in the pressure spindle (15) and extends from a central through bore (17) to the outside thereof.

7. The medical chuck (1) according to claim 1, wherein ft the second liquid flushing channel (26) extends from the flushing chamber (20) to and in fluid communication with the central liquid flushing passage (18).

8. The medical chuck (1) according to claim 1, wherein the drive element (15) is connected to the at least one clamping jaw (13).

9. The medical chuck (1) according to claim 1, wherein the second liquid flushing outflow channel (26) is axially spaced from the flushing first liquid flushing supply channel (21) for flushing the flushing chamber (20).

10. The medical chuck (1), according to claim 1, wherein the at least one clamping jaw (13) is provided with a mark (30) for indicating an adjustment position of the at least one clamping jaw (13) for cleaning the chuck (1).

11. The medical chuck (1) according to claim 1, wherein the removable hollow flushing wand or nozzle (24, 24') includes at one end a connecting section (35) for connection to a flushing fluid supply line, the removable hollow flushing wand or nozzle (24, 24') having a tube extension (36) at the opposite end which extends from a support surface (37) for supporting the medical chuck (1) during the flushing of the medical chuck (1).

12. A The medical chuck (1) according to claim 11, wherein a closing element (40) is supported on the removable hollow flushing wand or nozzle (24, 24') for closing a top end of the central liquid flushing passage (18) extending through the medical chuck (1) during the flushing of the medical chuck (1).

13. A medical chuck (1) for medical apparatus including rotating tools for use on a patient, comprising a housing (2) having an interior having spaces that may become contaminated during use of the medical chuck (1), at least one clamping jaw (13) movably supported in the housing (2) and means for moving the at least one clamping jaw (13) into, and out of, clamping positions extending beyond the housing (2) and including at least one drive element (15, 6), the means for moving the at least one clamping jaw (13) housed within the housing (2), means for hygienically liquid flushing the medical chuck (1) including all of the spaces of the interior of the housing (2), the at least one clamping jaw (13) and the at least one drive element (15, 6) of retained bodily liquids and tissues of a patient after use of the medical chuck (1), wherein the means for hygienically liquid flushing the medical chuck (1) including all spaces of the interior of the housing (2), the at least one clamping jaw (13) and the at least one drive element (15, 6) of retained bodily liquids and tissues of a patient comprises the housing (2) having a central liquid flushing passage (18) extending axially therethrough, the at least one drive element (15, 6) at least partially surrounded by a liquid flushing chamber formed by a hollow space (20), the at least one drive element (15, 6) including at least one liquid flushing channel (21, 25, 26) in fluid communication between the central liquid flushing passage (18) and liquid flushing chamber (20), a removable hollow flushing wand or nozzle (24, 24') including an upper end having a first liquid discharge opening (27) in insertable relationship with the central liquid flushing passage (18) and upon insertion of the upper end of the removable hollow flushing wand or nozzle (24, 24') in the central liquid flushing passage (18) the first liquid discharge opening (27) in liquid communication with the central liquid flushing passage (18) and at least the hollow space (20), the removable hollow flushing wand or nozzle (24, 24') for insertion in the central liquid flushing passage (18) after use of the medical chuck (1) on the patient for carrying hygienic flushing liquid for thorough hygienic liquid flushing of the medical chuck (1) of retained bodily liquids and tissues of the patient including all spaces of the interior of the housing (2) and, the central liquid flushing passage (18) having a widened circumferential section at least for a portion of its axial length for forming an outer channel around the outer circumference of the removable hollow flushing wand (24, 24') for a predetermined portion of its length in the operative position, the outer channel for carrying the flushing fluid exterior to and in a direction at least about parallel to the flushing fluid passing through the removable hollow flushing wand (24, 24') during flushing of the medical chuck (1).

14. The medical chuck (1) of claim 13, wherein the removable hollow flushing wand or nozzle (24, 24') further includes at its circumference at least one or several additional flushing liquid discharge openings (28) in predetermined position and in fluid communication with the outer channel of the central liquid flushing passage (18).

15. A method of cleaning a medical chuck (1) for medical apparatus, the medical chuck (1) including rotating tools for use on a patient, comprising a housing (2) having an interior having spaces that may become contaminated during use of the medical chuck (1), at least one clamping jaw (13) movably supported in the housing (2) and means for moving the at least one clamping jaw (13) into, and out of, clamping positions extending beyond the housing (2) and including at least one drive element (15, 6), the means for moving the at least one clamping jaw (13) housed within the housing (2), means for hygienically liquid flushing the medical chuck (1) including all of the spaces of the interior of the housing (2), the at least one clamping jaw (13) and the at least one drive element (15, 6) of retained bodily liquids and tissues of a patient after use of the medical chuck (1), the housing (2) having a central liquid flushing passage (18) extending axially therethrough, the at least one drive element (15, 6) at least partially surrounded by a liquid flushing chamber formed by a hollow space (20), the at least one drive element (15, 6) including at least one liquid flushing channel (21, 25, 26) in fluid communication between the central liquid flushing passage (18) and liquid flushing chamber (20), a removable hollow flushing wand or nozzle (24, 24') including an upper end having a first liquid discharge opening (27) in insertable relationship with the central liquid flushing passage (18) and upon insertion of the upper end of the removable hollow flushing wand or nozzle (24, 24') in the central liquid flushing passage (18) the first liquid discharge opening (27) in liquid communication with the central liquid flushing passage (18) and at least the liquid flushing chamber (20), the removable hollow flushing wand (24, 24') for insertion in the central liquid flushing passage (18) after use of the medical chuck (1) on the patient for carrying hygienic flushing liquid for thorough hygienic liquid flushing of the medical chuck (1) of retained bodily liquids and tissues of the patient including all spaces of the interior of the housing (2), a step (23) in operative position in the central liquid flushing passage (18), the removable hollow flushing wand or nozzle (24, 24') upon insertion into the central liquid flushing passage (18) in seated relationship with the step (23), the step (23) is formed axially between first and second liquid flushing channels (21 and 26), and, a first liquid flushing supply channel (21) is a flushing liquid supply channel and a second liquid flushing channel (26) is a flushing liquid outflow channel, said method comprising the step of conducting a flushing liquid through the liquid flushing chamber (20) via the first liquid flushing supply channel (21) and out of the liquid flushing chamber (20) via the second flushing liquid outflow channel (26) spaced from the first liquid flushing fluid supply channel (21).

16. A method of cleaning a chuck (1) according to claim 15, wherein for cleaning, the chuck (1) is removed from the medical apparatus, the at least one clamping jaw (13) is moved to a marked cleaning position and is then placed onto the removable hollow flushing wand or nozzle (24, 24') and flushing fluid is supplied to the chuck (1) via the removable hollow flushing wand or nozzle (24, 24').

* * * * *